March 29, 1960 J. P. TREMMEL ET AL Plant Pat. 1,925
PEACH TREE
Filed Sept. 12, 1958
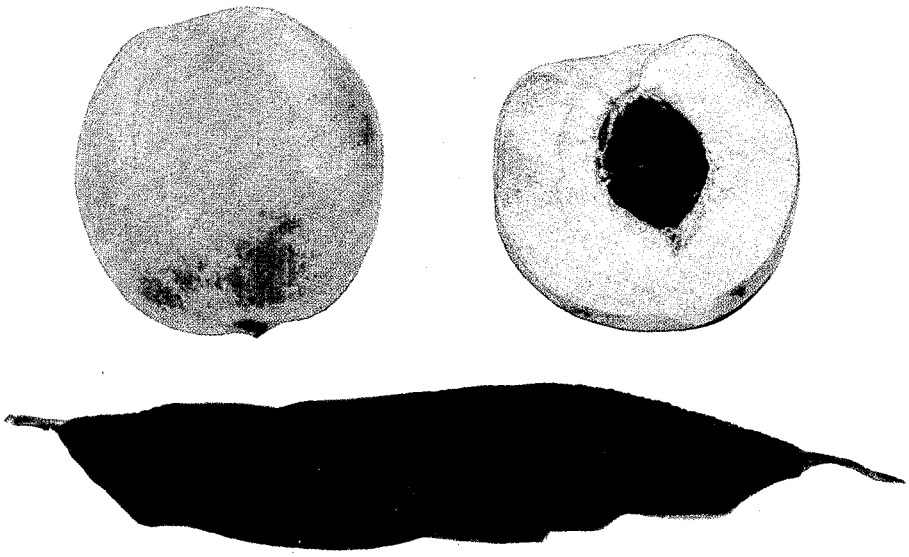
INVENTORS
John P. Tremmel & Minnie K. Tremmel
By Orville M. Kile
Plant Patent Agent United States Patent Office Plant Pat. 1,925
Patented Mar. 29, 1960

1,925

PEACH TREE

John P. Tremmel and Minnie K. Tremmel,
near Sigourney, Iowa

Application September 12, 1958, Serial No. 760,821

1 Claim. (Cl. 47—62)

Our present invention relates to a new and distinct variety of peach tree, which originated as a seedling on our farm. Outstanding among its qualities are its great resistance to cold, and its heavy production of fruit of good size, excellent flavor and texture, for use particularly in canning or freezing.

This new variety is of unknown parentage and was discovered on our farm near Sigourney, Iowa as a seedling where we had planted a number of seeds from various sources. It first came to our attention in the spring following a very severe winter. This new seedling had a 50% set of blossoms and fruit whereas other adjoining trees or others in the neighborhood had no blossoms beacuse of the severe winter. Severe drought and grasshopper infestation prevented ripening of peaches on our tree during that year, however.

In several subsequent seasons, after severe sub-zero weather, our variety bore a heavy crop of fruit with no damage to the budwood. Fruit buds of other varieties in the neighborhood, particularly the varieties Polly and Sun Gold (unpatented), were killed by the low temperatures and many trees were killed or their budwood badly damaged.

We therefore proceeded to asexually reproduce the variety by means of budding at our farm near Sigourney and found the outstanding qualities to be permanent.

The accompanying illustration is a color photograph of a whole peach, a half peach with seed, and a leaf, all in approximately natural size and colors in the original. However, size of both fruit and leaf will vary depending on the amount of thinning done, the position on the tree and the growing conditions.

In the following description, color designations refer to Ridgway's Color Standards and Nomenclature, except that where no plate references are given the ordinary dictionary meaning of the term is intended.

*The tree*

Growth: Medium in size. If topped when young it will grow into a spreading, symmetrical tree.

Bearing habits: Tree begins to bear very young and has a long life of production. (The original tree lived 16 years.) This variety produces a very heavy set of fruit and usually requires a 50% to 75% thinning in order to get a heavy crop of large-sized fruit.

Hardiness: This variety is extremely hardy to low winter temperatures. Often it sets peaches after a severe winter when most of the blossoms on all other varieties in the vicinity are killed. The original tree had several full crops of fruit following winters of below-zero weather—even as low as 22 degrees below zero, Fahrenheit.

Leaves:

*Size.*—Medium to large, varying in size but averaging about 6 inches long by 1½ inches wide.

*Type.*—Has reniform or kidney-shaped glands.

*Shape.*—Narrow elliptical, with long, sharp apex; edges shallowly serrate.

*Color.*—Dark green, approximately Elm Green (Pl. XVII).

*Petiole.*—Short.

*Appearance.*—Smooth; shiny; slightly undulate.

*Disease resistance.*—Very resistant to leaf curl. When other varieties (particularly Polly and Sun Gold) grown in similar circumstances were infected, our new variety had only a few leaves with slight curl at the edges.

Blossoms:

*Size.*—Large, usually 1½ inches in diameter.

*Color.*—Pale pink to dark pink.

*Type.*—Self-pollinating.

*Season.*—Mid-April to May 1 in this vicinity.

*The fruit*

Form: Globular, with deep basin. Nearly symmetrical. Uniform.

Size: From 2½ to 3 inches in diameter, if tree is properly thinned (50 to 75%).

Maturity: Fruit usually starts ripening about August 20 in this area although the season varies somewhat according to weather conditions.

Ripening habit: Fruit colors one-half to two-thirds red a week or ten days before ripe. Does not drop easily when ripe.

Uses: Especially good for canning and freezing.

Keeping and shipping qualities: Excellent if picked in hard-ripe condition.

Skin:

*Color.*—Basic color lies between Primuline Yellow (Pl. XVI) and Yellow Ochre (Pl. XV). More than half of this basic color is covered with an over-all red which is between Carmine and Garnet Brown (Pl. I), being very red on the side which has been next the sunlight.

*Adherence.*—Skin separates easily when fruit is ripe.

*Pubescence.*—Average amount of fuzz is present.

Flesh:

*Color.*—Yellow (approximately Empire Yellow, Pl. IV), with slight red markings around the pit.

*Texture.*—Firm but tender. Ships well when picked in hard-ripe stage.

*Fibers.*—Few.

*Flavor.*—Excellent; sub-acid to sweet.

Stone:

*Type.*—Completely free under normal conditions of ripening.

*Size.*—Medium to small.

*Surface.*—Deeply pitted.

*Form.*—Plump.

*Color.*—Approximately Nopal Red (Pl. I).

Having thus disclosed our discovery, we claim:

The freestone peach tree substantially as herein shown and described, characterized particularly by its great resistance to cold; its early and long bearing of fruit; its resistance to leaf curl; its heavy production of blossoms and fruit; and its relatively large fruit of firm, excellent-flavored, yellow flesh and attractive, early red coloring of its skin.

No references cited.